(12) United States Patent
Li et al.

(10) Patent No.: US 9,763,620 B2
(45) Date of Patent: Sep. 19, 2017

(54) HEAD MOUNTED SYSTEM

(71) Applicant: Quanta Computer Inc., Tao Yuan Shien (TW)

(72) Inventors: Chung-Te Li, New Taipei (TW); Wen-Chu Yang, New Taipei (TW)

(73) Assignee: QUANTA COMPUTER INC., Tao Yuan Shien (TW)

(*) Notice: Subject to any disclaimer, the term of this patent is extended or adjusted under 35 U.S.C. 154(b) by 861 days.

(21) Appl. No.: 14/134,653

(22) Filed: Dec. 19, 2013

(65) Prior Publication Data
US 2015/0087924 A1 Mar. 26, 2015

(30) Foreign Application Priority Data
Sep. 24, 2013 (TW) .............................. 102134353 A

(51) Int. Cl.
*A61B 5/00* (2006.01)
*A61B 5/1455* (2006.01)
(Continued)

(52) U.S. Cl.
CPC .......... *A61B 5/6803* (2013.01); *A61B 3/0041* (2013.01); *A61B 3/14* (2013.01);
(Continued)

(58) Field of Classification Search
None
See application file for complete search history.

(56) References Cited

U.S. PATENT DOCUMENTS 6,486,773 B1 11/2002 Bailie et al.
6,801,137 B2 10/2004 Eggers
(Continued)

FOREIGN PATENT DOCUMENTS

CN 2798135 Y 7/2006
CN 102137476 A 7/2011
(Continued)

OTHER PUBLICATIONS

Taiwanese Office Action dated Mar. 4, 2016.
(Continued)

*Primary Examiner* — G. Steven Vanni
(74) *Attorney, Agent, or Firm* — Rabin & Berdo, P.C.

(57) ABSTRACT

A head mounted system includes a physiological signal sensor, a signal processing circuit, a memory, an application processor, and an eyeglass frame. The physiological signal sensor monitors a physiological state to output a physiological signal. The signal processing circuit determines whether the physiological state is abnormal according to the physiological signal. When it is not abnormal, the signal processing circuit controls the physiological signal sensor to monitor the physiological state at a first monitoring frequency. When it is abnormal, the signal processing circuit outputs a warning signal, and controls the physiological signal sensor to monitor the physiological state at a second monitoring frequency greater than the first monitoring frequency. The application processor receives the warning signal and stores physiological data corresponding to the physiological signal in the memory. The eyeglass frame carries the first physiological signal sensor, the signal processing circuit, the memory, and the application processor.

11 Claims, 7 Drawing Sheets

(51) Int. Cl.
  *A61B 3/14* (2006.01)
  *A61B 5/0205* (2006.01)
  *A61B 5/021* (2006.01)
  *A61B 3/00* (2006.01)
  *G02B 27/01* (2006.01)
  *A61B 5/024* (2006.01)

(52) U.S. Cl.
  CPC ........ *A61B 5/0077* (2013.01); *A61B 5/02055* (2013.01); *A61B 5/02108* (2013.01); *A61B 5/14552* (2013.01); *G02B 27/017* (2013.01); *A61B 5/02416* (2013.01)

(56) References Cited

U.S. PATENT DOCUMENTS

| | | |
|---|---|---|
| 2001/0028309 A1 | 10/2001 | Torch |
| 2007/0276260 A1 | 11/2007 | Hammer et al. |
| 2008/0027502 A1 | 1/2008 | Ransom |
| 2012/0257164 A1 | 10/2012 | Zee et al. |
| 2013/0096439 A1 | 4/2013 | Lee et al. |

FOREIGN PATENT DOCUMENTS

| | | |
|---|---|---|
| CN | 103040452 A | 4/2013 |
| DE | 4434013 A1 | 4/1996 |
| JP | 2005-508215 A | 3/2005 |
| TW | 201247182 A | 12/2012 |

OTHER PUBLICATIONS

Chinese Office Action dated Aug. 18, 2016.
Chinese Office Action dated Nov. 7, 2016.
Taiwanese Office Action dated Dec. 21, 2015.

HEAD MOUNTED SYSTEM

This application claims the benefit of Taiwan application Serial No. 102134353, filed Sep. 24, 2013, the subject matter of which is incorporated herein by reference.

TECHNICAL FIELD

The invention relates in general to an electronic device, and more particularly to a head mounted system.

BACKGROUND

As technology progresses, people receive more information from electronic devices, such as multimedia players, network communication devices, and computers, which are equipped with display devices such as CRTs or LCDs for displaying images. The number of pixels and size of the image displayed by the display devices are constrained by the size of the display devices and their performance. Hence, the conventional CRT or LCD displays cannot meet the requirement of compact, portability, and a size with high display quality. For resolving this problem, the head-mounted display (HMD) is provided in the market. The head-mounted display provides one or two small tubes or LCDs disposed in front of the left and right eyes of a person. For example, a head-mounted display achieves stereoscopic effects by using binocular parallax, which projects images outputted from the tubes or LCDs through beam splitters onto the eyes of the user.

SUMMARY

The disclosure is directed to a head mounted system.

According to an embodiment, a head mounted system is provided. The head mounted system includes a physiological signal sensor, a signal processing circuit, a memory, an application processor, and an eyeglass frame. The physiological signal sensor monitors a physiological state to output a physiological signal. The signal processing circuit determines whether the physiological state is abnormal according to the physiological signal. When the physiological state is not abnormal, the signal processing circuit controls the physiological signal sensor to monitor the physiological state at a first monitoring frequency. When the physiological state is abnormal, the signal processing circuit outputs a warning signal, and controls the physiological signal sensor to monitor the physiological state at a second monitoring frequency. The second monitoring frequency is greater than the first monitoring frequency. The application processor receives the warning signal and stores physiological data corresponding to the physiological signal in the memory. The eyeglass frame carries the first physiological signal sensor, the signal processing circuit, the memory, and the application processor.

The above and other aspects of the invention will become better understood with regard to the following detailed description of the preferred but non-limiting embodiment(s). The following description is made with reference to the accompanying drawings.

DETAILED DESCRIPTION OF THE INVENTION

The following provides embodiments of a head mounted system. The head mounted system includes a physiological signal sensor, a signal processing circuit, a memory, an application processor, and an eyeglass frame. The physiological signal sensor monitors a physiological state to output a physiological signal. The physiological signal sensor, for example, is an image sensor, an infrared sensor, a pressure sensor, or a temperature sensor. The physiological state, for example, indicates a heart beat rate, retinopathy, vascular proliferation, blood oxygenation, a pulse pattern, or a body temperature. The signal processing circuit determines whether the physiological state is abnormal according to the physiological signal. When the physiological state is not abnormal, the signal processing circuit controls the physiological signal sensor to monitor the physiological state at a lower monitoring frequency. Conversely, when the physiological state is abnormal, the signal processing circuit outputs a warning signal to the application processor, and controls the physiological signal sensor to monitor the physiological state at a higher monitoring frequency. The application processor receives the warning signal, and stores physiological data corresponding to the physiological signal in the memory. For example, the physiological data indicates records of the heart beat rate, records of eyes, records of blood oxygenation, records of pulse patterns, or records of body temperature. The eyeglass frame carries the physiological signal sensor, the signal processing circuit, the memory, and the application processor. After receiving the warning signal, the application processor can, through a user interface, advise the user to go to see a doctor or do something for oneself.

First Embodiment

Figure 1:
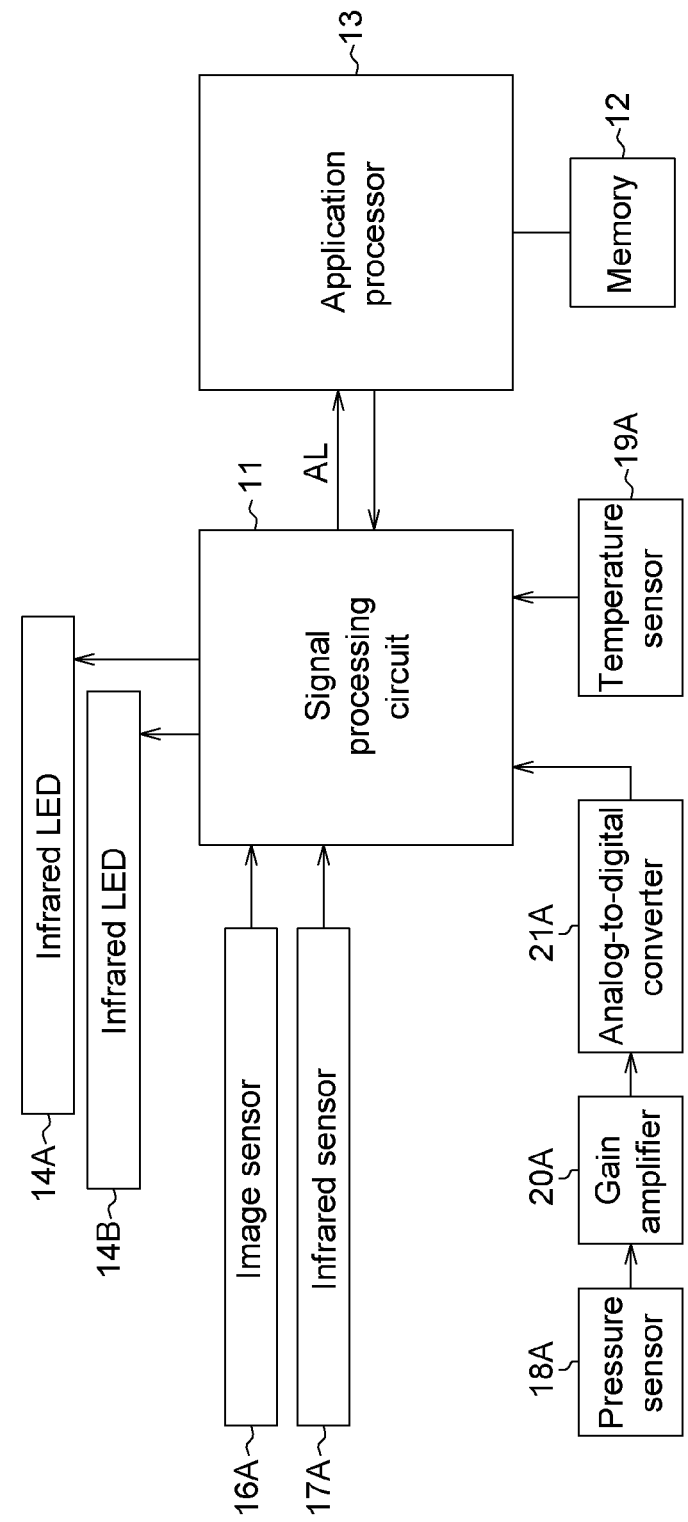
FIG. 1 is a block diagram of a head mounted system according to a first embodiment.
Figure 2:
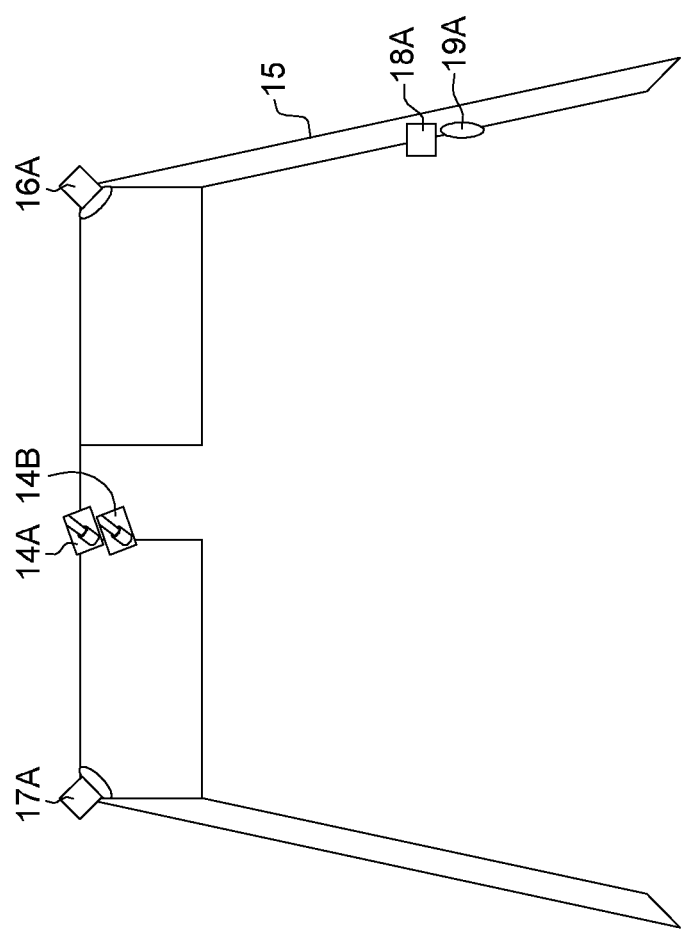
FIG. 2 is a diagram illustrating the appearance of a head mounted system according to the first embodiment.

Referring to FIGS. 1 and 2, FIG. 1 shows a head mounted system according to a first embodiment in a block diagram, and FIG. 2 illustrates the appearance of a head mounted system according to the first embodiment. The head mounted system 1 includes a physiological signal sensor, a signal processing circuit 11, a memory 12, an application processor 13, an infrared light emitting diode (LED) 14A, an infrared LED 14B, an eyeglass frame 15, a gain amplifier 20A, and an analog-to-digital converter 21A. For example, the signal processing circuit 11 is an application-specific integrated circuit (ASIC), and the signal processing circuit 11 communicates with the application processor 13 through a universal serial bus (USB). The wavelengths of the infrared LED 14A and the infrared LED 14B are different. For example, the wavelength of the infrared LED 14A is 750 nm, and the wavelength of the infrared LED 14B is 950 nm. The eyeglass frame 15 is utilized to carry the physiological signal sensor, the signal processing circuit 11, the memory 12, the application processor 13, the infrared LED 14A, the infrared LED 14B, the gain amplifier 20A, and the analog-to-digital converter 21A. The physiological signal sensor includes an image sensor 16A, an infrared sensor 17A, a pressure sensor 18A, and a temperature sensor 19A.

The image sensor 16A is employed to monitor a heart beat rate, retinopathy, or vascular proliferation. When the image sensor 16A monitors the heart beat rate, the physiological signal outputted by the image sensor 16A indicates an original image below the eyes. When the image sensor 16A monitors retinopathy or vascular proliferation, the physiological signal outputted by the image sensor 16A is an image of the eyes. The signal processing circuit 11 determines whether the heart beat rate is abnormal according to the original image below the eyes. When the heart beat rate is not abnormal, the signal processing circuit 11 controls the image sensor 16A to monitor the heart beat rate at a first monitoring frequency. Conversely, when the heart beat rate is abnormal, the signal processing circuit 11 outputs a warning signal AL to the application processor 13, and controls the image sensor 16A to monitor the heart beat rate at a second monitoring frequency. The second monitoring frequency is greater than the first monitoring frequency. After receiving the warning signal AL, the application processor 13 can inform the user through the user interface, wherein the user interface is a display device or a sound reproduction device, for example. The application processor 13 stores records of the heart beat rate in the memory 12.

Likewise, the signal processing circuit 11 determines whether the retinopathy or vascular proliferation is abnormal according to the image of the eyes. When the retinopathy or vascular proliferation is not abnormal, the signal processing circuit 11 controls the image sensor 16A to monitor the retinopathy or vascular proliferation at a first monitoring frequency. Conversely, when the retinopathy or vascular proliferation is abnormal, the signal processing circuit 11 outputs the warning signal AL to the application processor 13, and controls the image sensor 16A to monitor the retinopathy or vascular proliferation at a second monitoring frequency. The second monitoring frequency is greater than the first monitoring frequency. After receiving the warning signal AL, the application processor 13 can inform the user through the user interface, wherein the user interface is a display device or a sound reproduction device, for example. The application processor 13 stores records of the eyes in the memory 12.

It is noted that the first monitoring frequency may be set to a different value depending on the subject to be monitored. For example, the first monitoring frequency for monitoring the retinopathy or vascular proliferation is different from that for monitoring the heart beat rate. Similarly, the second monitoring frequency may be set to a different value depending on the subject to be monitored. For example, the second monitoring frequency for monitoring the retinopathy or vascular proliferation is different from that for monitoring the heart beat rate.

The infrared sensor 17A is employed to monitor the blood oxygenation. In this case, the physiological signal outputted by the infrared sensor 17A indicates a first image below the eyes of the user and a second image below the eyes of the user. The signal processing circuit 11 determines whether blood oxygenation is abnormal according to the first image below the eyes and the second image below the eyes. When the blood oxygenation is not abnormal, the signal processing circuit 11 controls the infrared sensor 17A to monitor the blood oxygenation at a third monitoring frequency. Conversely, when the blood oxygenation is abnormal, the signal processing circuit 11 outputs a warning signal AL to the application processor 13, and controls the infrared sensor 17A to monitor the blood oxygenation at a fourth monitoring frequency. The fourth monitoring frequency is greater than the third monitoring frequency. After receiving the warning signal AL, the application processor 13 can inform the user through the user interface, wherein the user interface is a display device or a sound reproduction device, for example. The application processor 13 stores records of the blood oxygenation in the memory 12.

The pressure sensor 18A is utilized to monitor the pulse pattern. In this case, the physiological signal outputted by the pressure sensor 18A indicates a pulse pattern signal. The signal processing circuit 11 determines whether the pulse pattern or blood pressure is abnormal according to the pulse pattern signal. When the pulse pattern is not abnormal, the signal processing circuit 11 controls the pressure sensor 18A to monitor the pulse pattern at a fifth monitoring frequency. Conversely, when the pulse pattern is abnormal, the signal processing circuit 11 outputs a warning signal AL to the application processor 13, and controls the pressure sensor 18A to monitor the pulse pattern at a sixth monitoring frequency. The sixth monitoring frequency is greater than the fifth monitoring frequency. After receiving the warning signal AL, the application processor 13 can inform the user through the user interface, wherein the user interface is a display device or a sound reproduction device, for example. The application processor 13 stores records of the pulse pattern in the memory 12.

The temperature sensor 19A is employed to monitor the body temperature. In this case, the physiological signal outputted by the temperature sensor 19A indicates a temperature signal. The signal processing circuit 11 determines whether the body temperature is abnormal according to the temperature signal. When the body temperature is not abnormal, the signal processing circuit 11 controls the temperature sensor 19A to monitor the pulse pattern at a seventh monitoring frequency. Conversely, when the body temperature is abnormal, the signal processing circuit 11 outputs a warning signal AL to the application processor 13, and controls the temperature sensor 19A to monitor the pulse pattern at an eighth monitoring frequency. The eighth monitoring frequency is greater than the seventh monitoring frequency. After receiving the warning signal AL, the application processor 13 can inform the user through the user interface, wherein the user interface is a display device or a sound reproduction device, for example. The application processor 13 stores records of the temperature in the memory 12.

Figure 3:
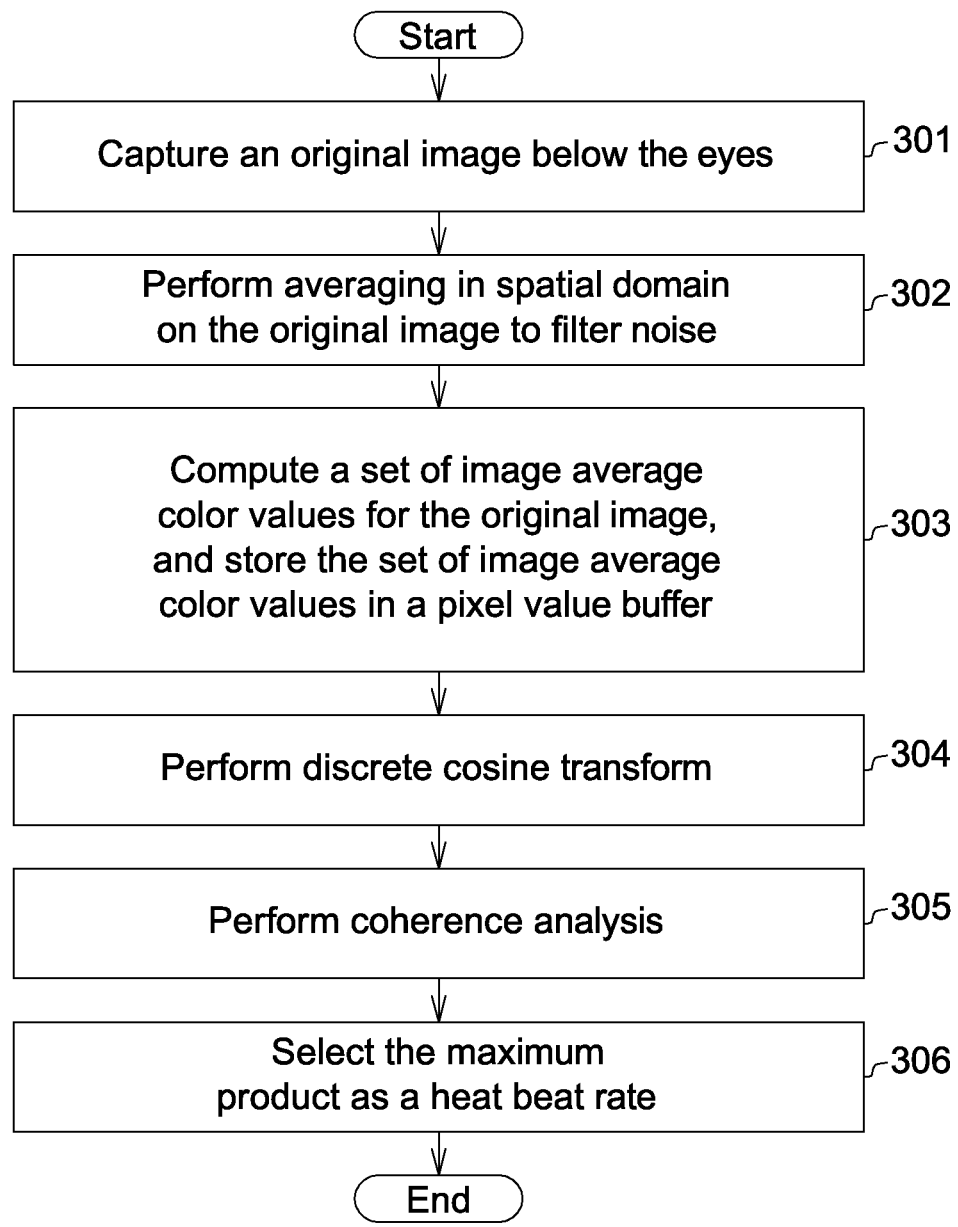
FIG. 3 is a flowchart of monitoring a heart beat rate according to the first embodiment.

Referring to FIGS. 1 and 3, FIG. 3 is a flowchart of monitoring a heart beat rate according to the first embodiment. First, in step 301, the image sensor 16A captures an original image below the eyes. If the brightness of the original image is too low, the infrared LED 14A or infrared LED 14B can be turned on to serve as an auxiliary light source. In step 302, the signal processing circuit 11 performs averaging in spatial domain on the original image to filter noise. The signal processing circuit 11 divides the original image into a plurality of image blocks, and performs averaging in spatial domain on the image blocks to filter noise.

After that, in step 303, the signal processing circuit 11 computes a set of image average color values for the original image, and stores the set of image average color values in a pixel value buffer. The signal processing circuit 11 calculates a set of block average color values for the image blocks, and stores the set of block average color values to the pixel value buffer. The set of image average color values include average pixel values with respect to lights of three different wavelengths. For example, the set of image average color values include an average red pixel value, an average green pixel value, and an average blue pixel value. Likewise, the set of block average color values also include an average red pixel value, an average green pixel value, and an average blue pixel value. The average red pixel value, the average green pixel value, and the average blue pixel value are stored to respective pixel value buffers. For example, if the image sensor 16A captures 30 images per second, and monitors the heart beat rate one time for at least 30 seconds, then the pixel value buffers store 900 sets of image average color values.

In step 304, the signal processing circuit 11 performs discrete cosine transform (DCT) on the image average color values to generate first DCT coefficients. The signal processing circuit 11 performs DCT on the block average color values to generate second DCT coefficients. Following that, in step 305, the signal processing circuit 11 performs coherence analysis according to the second DCT coefficients to generate a gain value. In step 306, the signal processing circuit 11 then performs multiplication of the second DCT coefficients and the gain value, and selects the maximum product as the heat beat rate.

Figure 4:
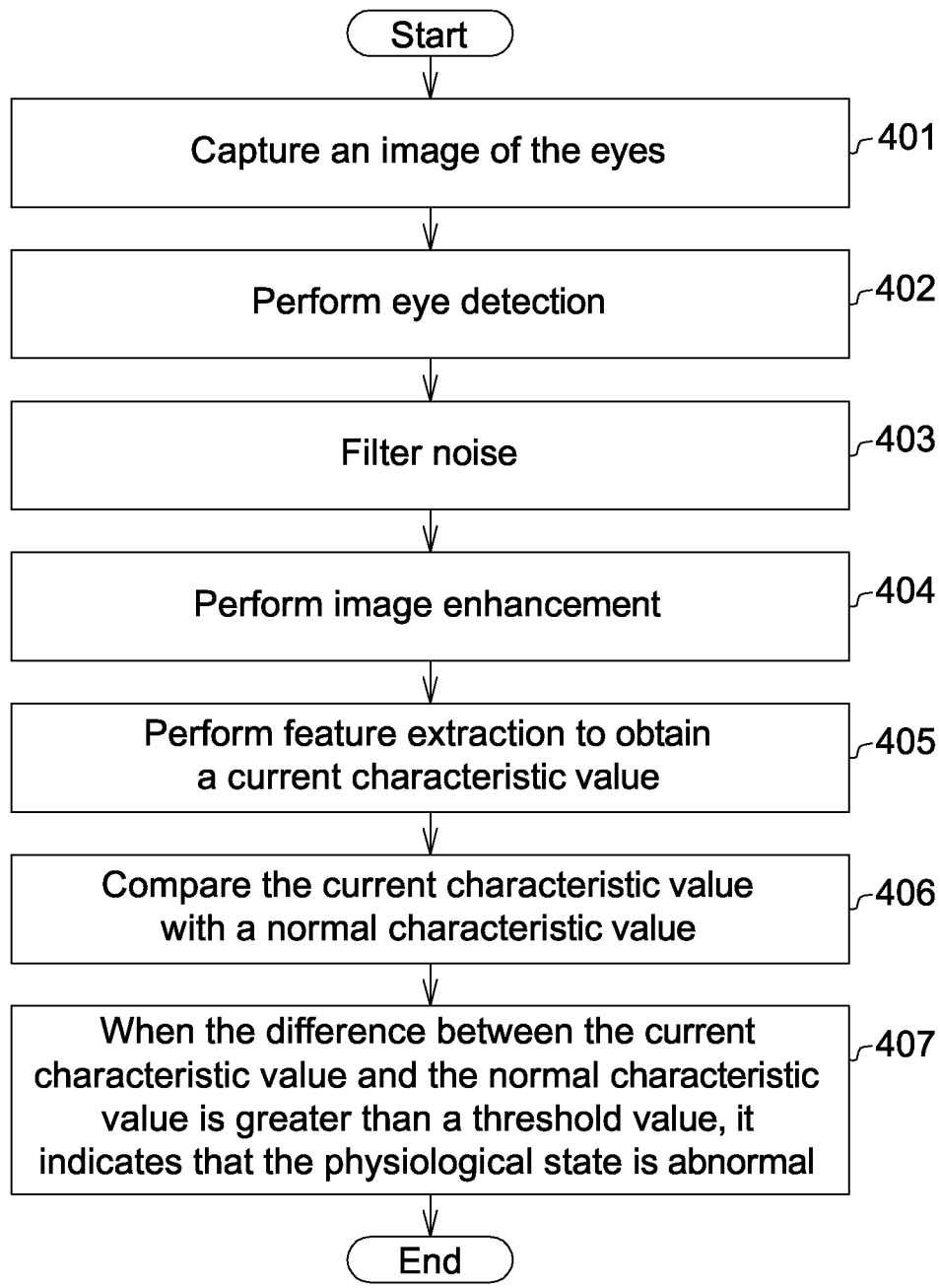
FIG. 4 is a flowchart of monitoring retinopathy or vascular proliferation according to the first embodiment.

Referring to FIGS. 1 and 4, FIG. 4 is a flowchart of monitoring retinopathy or vascular proliferation according to the first embodiment. First, in step 401, the image sensor 16A captures an image of the eyes. If the brightness of the original image is too low, the infrared LED 14A or infrared LED 14B can be turned on as an auxiliary light source. In step 402, the signal processing circuit 11 performs eye detection on the image of the eyes. The eye detection is performed in order to prevent the image sensor 16A from capturing an image of a wink. In step 403, the signal processing circuit 11 filters the noise of the image of the eyes. In step 404, the signal processing circuit 11 then performs image enhancement to generate a processed image. In step 405, the signal processing circuit 11 performs feature extraction on the processed image to obtain a current characteristic value. After that, in step 406, the signal processing circuit 11 compares the current characteristic value with a normal characteristic value. In step 407, when the difference between the current characteristic value and the normal characteristic value is greater than a threshold value, it indicates that the physiological state is abnormal.

Figure 5:
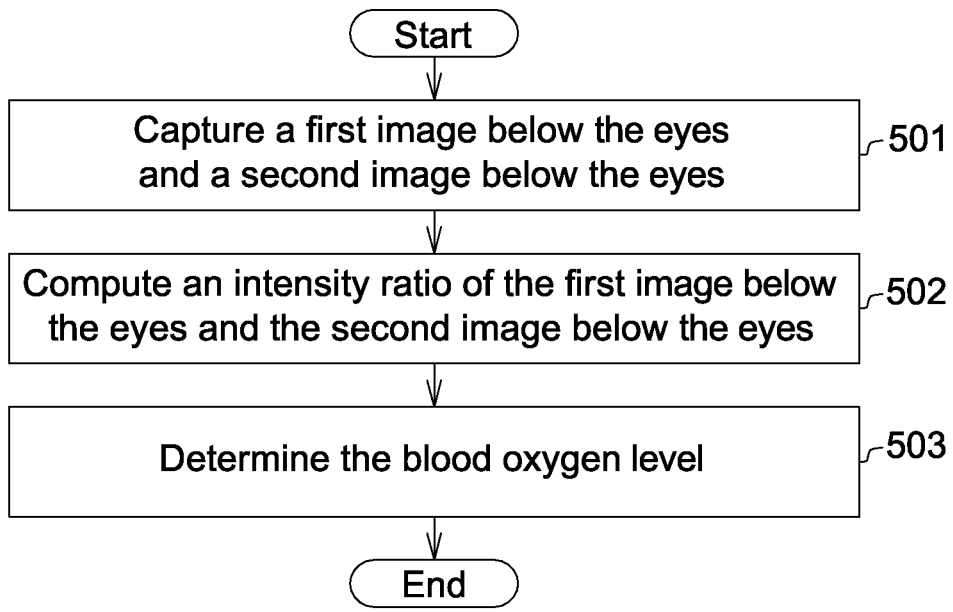
FIG. 5 is a flowchart of monitoring blood oxygenation according to the first embodiment.

Referring to FIGS. 1 and 5, FIG. 5 is a flowchart of monitoring blood oxygenation according to the first embodiment. First, in step 501, the signal processing circuit 11 turns on the infrared LED 14A and turns off the infrared LED 14B so as to enable the infrared sensor 17A to capture a first image below the eyes, and the signal processing circuit 11 turns on the infrared LED 14B and turns off the infrared LED 14A so as to enable the infrared sensor 17A to capture a second image below the eyes. After that, in step 502, the signal processing circuit 11 calculates the intensity ratio of the first image below the eyes and the second image below the eyes. In step 503, the signal processing circuit 11 then determines the blood oxygen concentration according to the intensity ratio. It is noted that the blood oxygen concentration can be determined since the absorptivity for infrareds of different wavelengths is different under different blood oxygenation levels.

Figure 6:
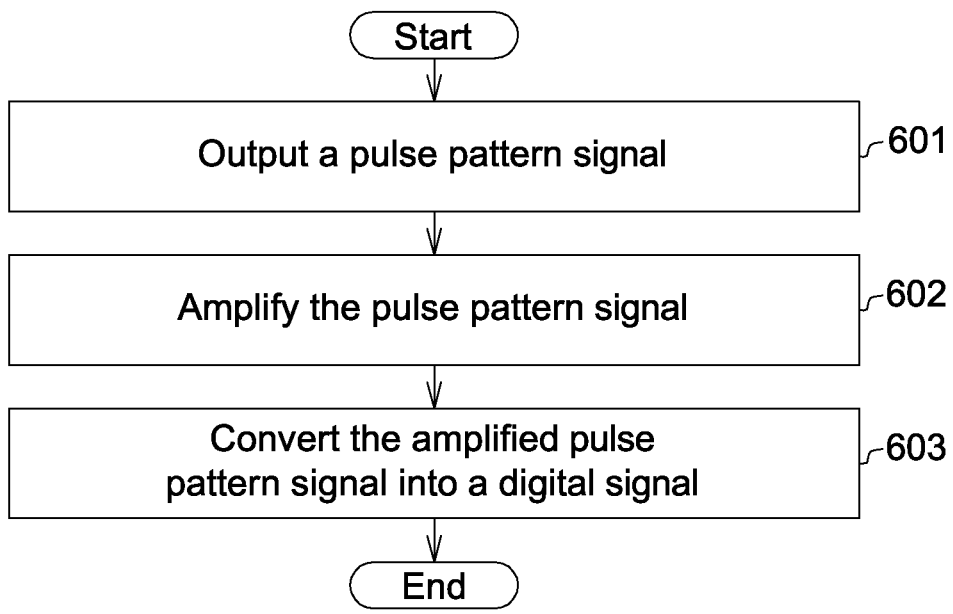
FIG. 6 is a flowchart of monitoring pulse pattern according to the first embodiment.

Referring to FIGS. 1 and 6, FIG. 6 is a flowchart of monitoring pulse pattern according to the first embodiment. First, in step 601, the pressure sensor 18A outputs a pulse pattern signal (pulse pattern as in traditional Chinese medicine). In step 602, the gain amplifier 20A amplifies the pulse pattern signal. In step 603, the analog-to-digital converter 21A converts the amplified pulse pattern signal into a digital signal and outputs the digital signal to the signal processing circuit 11. In addition, the signal processing circuit 11 can first calculate a matching value in an initial calibration mode according to a peak value and a valley value of the pulse pattern signal, an initial systolic pressure value, and an initial diastolic pressure value. The initial systolic pressure value and the initial diastolic pressure value of a user can be measured by using a blood-pressure meter. The signal processing circuit 11 can then compute a current systolic pressure value and a current diastolic pressure in a measurement mode according to the pulse pattern signal and the matching value.

For example, a blood-pressure meter measures an initial systolic pressure value B1 and an initial diastolic pressure value B2 for a user. Meanwhile, the peak value of the pulse pattern signal is A1 and the valley value of the pulse pattern signal is A2. The signal processing circuit 11 calculates a matching value $$K = \frac{B1 - B2}{A1 - A2}$$

in an initial calibration mode. After that, the pulse pattern signal outputted by the pressure sensor 18A has a peak value of C1 and a valley value of C2. The signal processing circuit 11 calculates the user's current systolic pressure by B1+K (C1−A1) and current diastolic pressure by B2+K(C2−A2).

Second Embodiment

Figure 7:
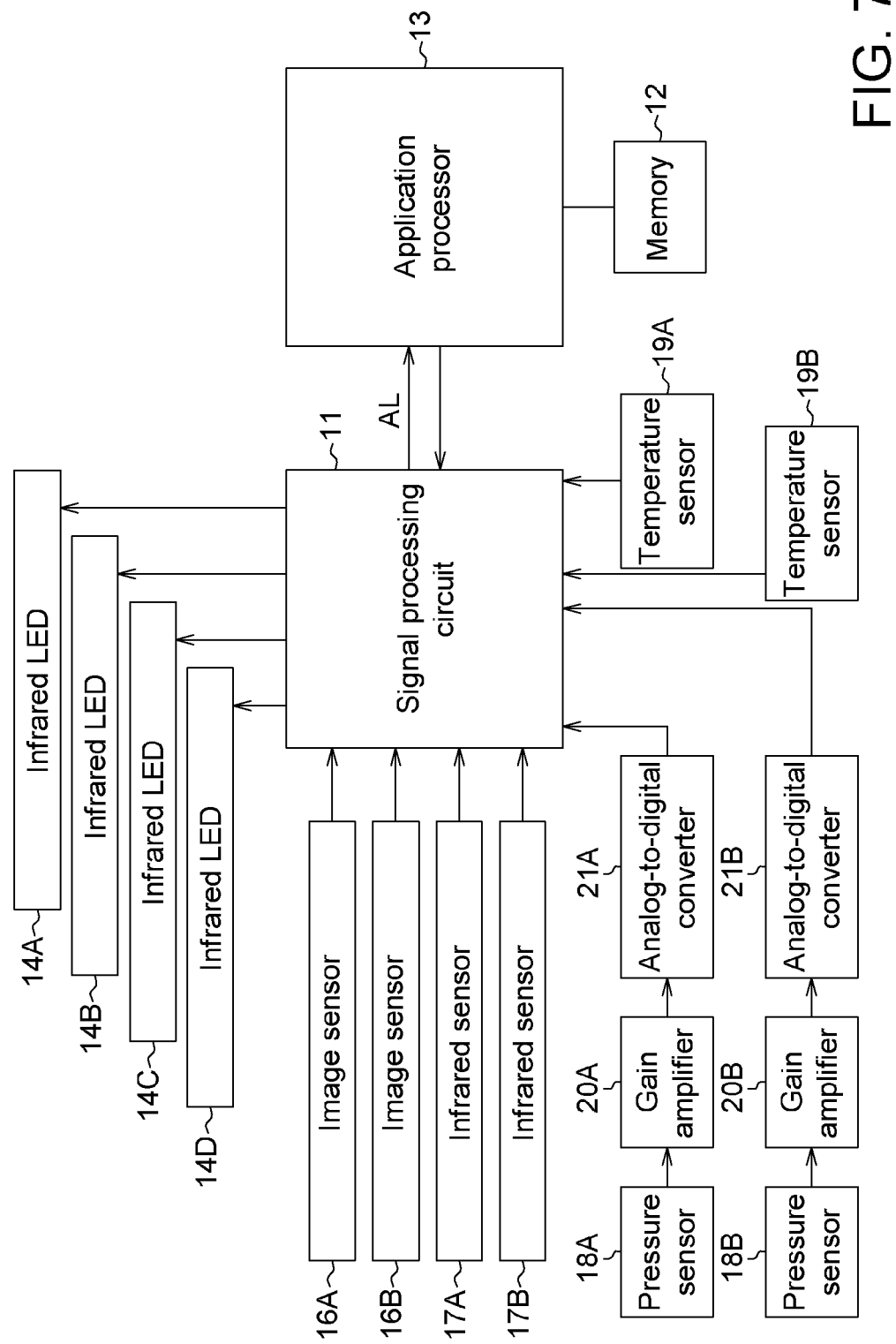
FIG. 7 is a block diagram of a head mounted system according to a second embodiment.
Figure 8:
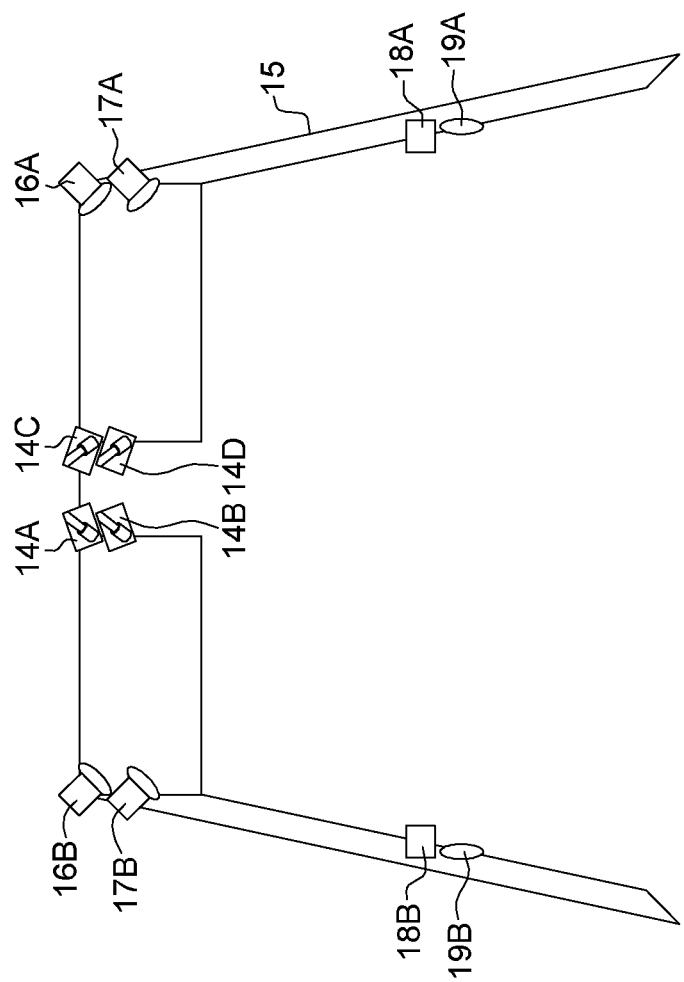
FIG. 8 is a diagram illustrating the appearance of a head mounted system according to the second embodiment.

Referring to FIGS. 7 and 8, FIG. 7 shows a block diagram of a head mounted system according to a second embodiment and FIG. 8 illustrates the appearance of a head mounted system according to the second embodiment. The second embodiment differs from the first embodiment in that the second embodiment further includes an infrared LED 14C, an infrared LED 14D, an image sensor 16B, an infrared sensor 17B, a pressure sensor 18B, a temperature sensor 19B, a gain amplifier 20B, and an analog-to-digital converter 21B. The wavelength of the infrared LED 14C is different from that of the infrared LED 14D. The eyeglass frame 15 further carries the infrared LED 14C, the infrared LED 14D, the image sensor 16B, the infrared sensor 17B, the pressure sensor 18B, the temperature sensor 19B, the gain amplifier 20B, and the analog-to-digital converter 21B.

The image sensor 16A is employed to monitor the heart beat rate, retinopathy, or vascular proliferation. When the image sensor 16B monitors the heart beat rate, the physiological signal outputted by the image sensor 16B indicates an original image below the eyes. When the image sensor 16B monitors the retinopathy or vascular proliferation, the physiological signal outputted by the image sensor 16B indicates the image of the eyes.

The infrared sensor 17B is utilized to monitor the blood oxygenation. In this case, the physiological signal outputted by the infrared sensor 17B indicates a first image below the eyes and a second image below the eyes. The pressure sensor 18B is used to monitor the pulse pattern. The physiological signal outputted by the pressure sensor 18B indicates the pulse pattern. The temperature sensor 19B is utilized to monitor body temperature. The physiological signal outputted by the temperature sensor 19B indicates the body temperature. The wavelength of the infrared LED 14C is different from that of the infrared LED 14D, and the infrared LED 14C and the infrared LED 14D are used for providing infrared lights. When the brightness of the original image is too low, the infrared LED 14A, 14B, 14C, or 14D can be turned on to serve as an auxiliary light source. The gain amplifier 20B is used for amplifying the pulse pattern signal outputted by the pressure sensor 18B. The analog-to-digital converter 21B converts the amplified pulse pattern signal into a digital signal and outputs the digital signal to the signal processing circuit 11.

While the invention has been described by way of example and in terms of the preferred embodiment(s), it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A head mounted system, comprising:
   a first physiological signal sensor, for monitoring a first physiological state to output a first physiological signal;
   a signal processing circuit, for determining whether the first physiological state is abnormal according to the first physiological signal, wherein
      when the first physiological state is not abnormal, the signal processing circuit controls the first physiological signal sensor to monitor the first physiological state at a first monitoring frequency,
      when the first physiological state is abnormal, the signal processing circuit outputs a first warning signal, and controls the first physiological signal sensor to monitor the first physiological state at a second monitoring frequency, and
      the second monitoring frequency is greater than the first monitoring frequency;
   a memory;
   an application processor, for receiving the first warning signal and storing first physiological data corresponding to the first physiological signal in the memory;
   an eyeglass frame, for carrying the first physiological signal sensor, the signal processing circuit, the memory, and the application processor;
   a second physiological signal sensor, mounted on the glass frame for monitoring a second physiological state to output a second physiological signal, wherein
      the signal processing circuit determines whether the second physiological state is abnormal according to the second physiological signal,
      when the second physiological state is not abnormal, the signal processing circuit controls the second physiological signal sensor to monitor the second physiological state at a third monitoring frequency,
      when the second physiological state is abnormal, the signal processing circuit outputs a second warning signal to the application processor, and controls the second physiological signal sensor to monitor the second physiological state at a fourth monitoring frequency, and
      the fourth monitoring frequency is greater than the third monitoring frequency;
   a third physiological signal sensor, mounted on the glass frame for monitoring a third physiological state to output a third physiological signal, wherein
      the signal processing circuit determines whether the third physiological state is abnormal according to the third physiological signal,
      when the third physiological state is not abnormal, the signal processing circuit controls the third physiological signal sensor to monitor the third physiological state at a fifth monitoring frequency,
      when the third physiological state is abnormal, the signal processing circuit outputs a third warning signal to the application processor, and controls the third physiological signal sensor to monitor the third physiological state at a sixth monitoring frequency, and
      the sixth monitoring frequency is greater than the fifth monitoring frequency; and
   a fourth physiological signal sensor, mounted on the glass frame for monitoring a fourth physiological state to output a fourth physiological signal, wherein
      the signal processing circuit determines whether the fourth physiological state is abnormal according to the fourth physiological signal,
      when the fourth physiological state is not abnormal, the signal processing circuit controls the fourth physiological signal sensor to monitor the fourth physiological state at a seventh monitoring frequency,
      when the fourth physiological state is abnormal, the signal processing circuit outputs a fourth warning signal to the application processor, and controls the fourth physiological signal sensor to monitor the fourth physiological state at an eighth monitoring frequency, and
      the eighth monitoring frequency is greater than the seventh monitoring frequency;
   wherein the first physiological signal sensor is a visible light imaging sensor, the second physiological signal sensor is an infrared imaging sensor, the third physiological signal sensor is a pressure sensor, and the fourth physiological signal sensor is a temperature sensor.

2. The head mounted system according to claim 1, wherein
   the first physiological state is a heart beat rate;
   the first physiological signal sensor captures a plurality of original images below the eyes;
   the signal processing circuit computes a set of image average color values for the original images below the eyes, performs discrete cosine transform (DCT) on the set of image average color values to generate a plurality of first DCT coefficients;
   the signal processing circuit divides the original images into a plurality of image blocks, and computes a plurality of sets of block average color values;
   the signal processing circuit performs DCT on the sets of block average color values to generate a plurality of second DCT coefficients, and compute the heart beat rate according to the second DCT coefficients and the first DCT coefficients.

3. The head mounted system according to claim 1, wherein
   the first physiological state indicates retinopathy or vascular proliferation, and the first physiological signal is an image of the eyes;
   the signal processing circuit performs eye detection, noise reduction, and image enhancement on the image of the eyes to generate a processed image, and performs feature extraction on the processed image to obtain a current characteristic value, and compares the current characteristic value with a normal characteristic value, when a difference between the current characteristic value with the normal characteristic value is greater than a threshold value, it indicates that the first physiological state is abnormal, wherein the retinopathy or vascular proliferation is indicated according to results of the performance of the signal processing circuit.

4. The head mounted system according to claim 1, further comprising:
- a first infrared light emitting diode (LED) mounted on the glass frame; and
- a second infrared LED mounted on the glass frame, wherein the first infrared LED and the second infrared LED, coupled to the signal processing circuit, are for providing infrared lights at different wavelengths for the second physiological signal sensor.

5. The head mounted system according to claim 4, wherein the second physiological state indicates blood oxygenation, the second physiological signal includes a first image below eyes and a second image below eyes;
- when the signal processing circuit turns on the first infrared LED and turns off the second infrared LED, the second physiological signal sensor outputs the first image below the eyes;
- when the signal processing circuit turns on the second infrared LED and turns off the first infrared LED, the second physiological signal sensor outputs the second image below the eyes;
- the signal processing circuit computes an intensity ratio of the first image below the eyes and the second image below the eyes, and computes the blood oxygenation according to the intensity ratio.

6. The head mounted system according to claim 1, wherein the third physiological state indicates a pulse pattern, and the third physiological signal includes a pulse pattern signal.

7. The head mounted system according to claim 6, further comprising:
- a first gain amplifier, mounted on the glass frame for amplifying the pulse pattern signal; and
- a first analog-to-digital converter, mounted on the glass frame for converting the amplified pulse pattern signal into a first digital signal and outputting the first digital signal to the signal processing circuit.

8. The head mounted system according to claim 6, wherein the signal processing circuit in an initial calibration mode computes a matching value according to a peak value and a valley value of the pulse pattern signal, an initial systolic pressure value, and an initial diastolic pressure value;
- the signal processing circuit in a measurement mode computes a current systolic pressure value and a current diastolic pressure value according to the pulse pattern signal and the matching value.

9. The head mounted system according to claim 1, wherein the fourth physiological state indicates body temperature, and the fourth physiological signal includes a temperature signal.

10. The head mounted system according to claim 1, further comprising:
- a fifth physiological signal sensor, mounted on the glass frame for monitoring the first physiological state to output a fifth physiological signal;
- a sixth physiological signal sensor, mounted on the glass frame for monitoring the second physiological state to output a sixth physiological signal;
- a seventh physiological signal sensor, mounted on the glass frame for monitoring the third physiological state to output a seventh physiological signal;
- an eighth physiological signal sensor, mounted on the glass frame for monitoring the fourth physiological state to output an eighth physiological signal;
- a third infrared LED mounted on the glass frame; and
- a fourth infrared LED mounted on the glass frame, wherein the third infrared LED and the fourth infrared LED provide infrared lights at different wavelengths.

11. The head mounted system according to claim 10, further comprising:
- a second gain amplifier, mounted on the glass frame for amplifying the seventh physiological signal; and
- a second analog-to-digital converter, mounted on the glass frame for converting the amplified seventh physiological signal into a second digital signal and output the second digital signal to the signal processing circuit.

* * * * *